(12) United States Patent
Dupau et al.

(10) Patent No.: US 8,003,838 B2
(45) Date of Patent: Aug. 23, 2011

(54) 1,4-HYDROGENATION OF DIENES WITH RU COMPLEXES

(75) Inventors: Philippe Dupau, Bellegarde (FR); Lucia Bonomo, Bellegarde (FR)

(73) Assignee: Firmenich SA, Geneva (CH)

( * ) Notice: Subject to any disclaimer, the term of this patent is extended or adjusted under 35 U.S.C. 154(b) by 148 days.

(21) Appl. No.: 12/530,760

(22) PCT Filed: Apr. 2, 2008

(86) PCT No.: PCT/IB2008/051227
§ 371 (c)(1),
(2), (4) Date: Jun. 10, 2009

(87) PCT Pub. No.: WO2008/120175
PCT Pub. Date: Oct. 9, 2008

(65) Prior Publication Data
US 2010/0099904 A1 Apr. 22, 2010

(30) Foreign Application Priority Data
Apr. 3, 2007 (EP) ..................................... 07105554

(51) Int. Cl.
*C07C 5/02* (2006.01)
*C07F 15/00* (2006.01)
(52) U.S. Cl. ......... 585/257; 568/687; 568/903; 556/136
(58) Field of Classification Search .................. 556/136; 568/687, 903; 585/275
See application file for complete search history.

(56) References Cited

FOREIGN PATENT DOCUMENTS
EP 1 394 170 3/2004
WO WO 2006/051503 5/2006

OTHER PUBLICATIONS

Mbaye et al., Journal of Organometallic Chemistry, vol. 690, pp. 2149-2158 (2005).*
Niessen et al., Magn. Reson. Chem., vol. 38, pp. 747-750 (2000).*
International Search Report, PCT/IB2008/051227, mailed Aug. 28, 2008.
Alvarez, Patricia et al., "Synthesis and Reactivity of Indenyl Ruthenium (II) Complexes Containing the Labile Ligand 1,5-Cyclooctadiene (COD): Catalytic Activity of [Ru($\eta^5$—$C_9H_7$)Cl(COD)]", Oragnometallics, vol. 20, pp. 3762-3771, (2001).
Bouachir, Faouzi, et al., XP-000984345, "Preparation and Stoichiometric and Catalytic Reactivity of Hydrido Organometallic Ruthenium Complexes. X-ray Crystal Structure of [RuH($\eta^5$—$C_8H_{11}$)$_2$]BF$_4$", Organometallics, vol. 10, pp. 455-462, (1991).
Dehmlow, Eckehard, V., et al., "Verbesserte Präparative Darstellung von Polyisopropyl-und Poly-*tert*-butylcyclopentadienen [1]" (1993).
Drießen-Hölscher, Birgit, et al., XP004144854, "Selective Two-Phase-Hydrogenation of Sorbic Acid with Novel Water Soluble Ruthenium Complexes", Journal of Organomettalic Chemistry, vol. 570, pp. 141-146, (1998).
Fagan, Paul J., et al., "Molecular Engineering of Solid-State Materials: Organomettalic Building Blocks", Journal Am. Chem. Soc., vol. 111, pp. 1698-1719, (1989).
Fagan, Paul J., et al., "Structure and Chemistry of the Complex Tetrakis($\eta^5$—pentamethylcyclopentadienyl)tetrakis($\mu_3$—chloro)-tetraruthenium(II): A Useful Precursor to (Pentamethylcyclopentadienyl)ruthenium(0), -(II), and -(IV) Complexes", Organometallics, vol. 9, pp. 1843-1852, (1990).
Rondon, Deyanira, et al., XP-002451878, "Carbon-Hydrogen, Carbon-Oxygen, and Carbon-Carbon Bond Activation by an Electrophilic Ruthenium Complex", Journal Am. Chem. Soc., vol. 113, pp. 5671-5676, (1991).
Steines, Stephan et al., XP-002256043, "Stereoselective Catalytic Hydrogenation of Sorbic Acid and Sorbic Alcohol with New Cp*Ru Complexes", The Royal Society of Chemistry, pp. 217-218, (2000).
Xue, Peng, et al., XP-002451877, "Reactions of [Cp*Ru(H$_2$O)(NBD)$^+$ with Dihydrogen, Silanes, Olefins, Alkynes, and Allenes", Organometallics, vol. 25, pp. 2344-2354, (2006).

* cited by examiner

*Primary Examiner* — Porfirio Nazario Gonzalez
(74) *Attorney, Agent, or Firm* — Winston & Strawn LLP

(57) ABSTRACT

The present invention relates to the use of Ruthenium complexes having cyclopentadienyl derivatives and a diene as ligands, together with some acidic additives for improving the selectivity in the 1,4-hydrogenation of conjugated dienes into the corresponding "cis"-alkene as major product, i.e. wherein the two substituents in position 2,3 of the diene are in a cis configuration in the corresponding alkene.

9 Claims, No Drawings

1,4-HYDROGENATION OF DIENES WITH RU COMPLEXES

This application is a 371 filing of International Patent Application PCT/IB2008/051227 filed Apr. 2, 2008.

TECHNICAL FIELD

The present invention relates to the field of catalytic hydrogenation and, more particularly to the use of specific Ru complexes with cyclopentadienyl derivatives, as one of the ligands, in 1,4-hydrogenation processes for the reduction of dienes into the corresponding "cis"-alkene as major product, i.e. wherein the two substituents in position 2,3 of the diene are in a cis configuration in the corresponding alkene.

PRIOR ART

Selective 1,4-hydrogenation of conjugated dienes into their corresponding "cis"-alkene is a very interesting reaction in organic chemistry, since it renders accessible a number of compounds which are obtained in general with a poor selectivity.

One of the mandatory and characterizing elements of such processes is the catalyst or the catalytic system. The development of useful catalysts or catalytic systems for the 1,4-hydrogenation of diene into the corresponding "cis"-alkene is still an important, difficult and unpredictable task in chemistry, in particular because the chemical industry is always eager for higher selectivity, as well as to maintain a high conversion or yield.

From the prior art, it is known that sorbic acid can be hydrogenated into the corresponding "cis"-alkene in the presence of [(Cp*)RuCO(phosphine)](anion) or [(Cp*)RuCO (sorbic acid)](anion) complexes, (see Driessen et al, in Chem. Commun., 2000, 217 or in J. Organomet. Chem, 1998, 141), however the yields (conversions×selectivity) are quite low.

Furthermore, in EP 1394170, it is reported the cisoid hydrogenation of dienes using as catalytic systems the complex [(Dienyl)Ru(acyclic diene)](anion) (in particular [(Cp*) Ru(sorbic acid)](anion) or [(Cp*)Ru(sorbol)](anion). In this document it is expressively shown that the use of cyclic diene, instead of acyclic diene, is highly detrimental to the overall yield. The only conditions displayed as providing good yields require nitromethane as solvent, the latter being relatively toxic and hazardous for industrial applications. Finally, Table 4 of said document shows that the addition of Lewis acids is highly detrimental to the yields.

Therefore, there is a need for processes using alternative catalytic systems possibly providing high selectivity and/or conversions.

DESCRIPTION OF THE INVENTION

In order to overcome the problems aforementioned, the present invention relates to processes for the catalytic reduction by 1,4-hydrogenation, using molecular $H_2$, of a conjugated diene (I) into the corresponding "cis"-alkene (II), characterized in that said process is carried out in the presence of at least an acidic additive of the type specified further below, the catalyst or pre-catalyst being a ruthenium complex comprising as ligand a cyclopentadienyl derivative.

The invention's process is shown in Scheme 1:

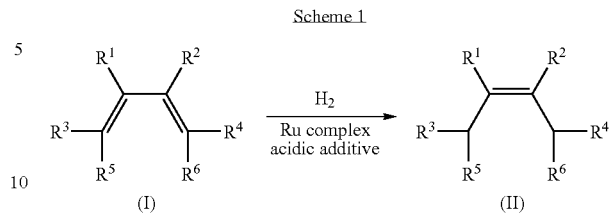

wherein the $R^1$ to $R^6$ are the substituents of the diene and of the alkene and wherein in compound (II) the $R^1$ and $R^2$ groups are in a cis configuration.

A particular embodiment of the invention is a process for the catalytic reduction by 1,4-hydrogenation, using molecular $H_2$, of a $C_5$-$C_{22}$ conjugated diene of formula

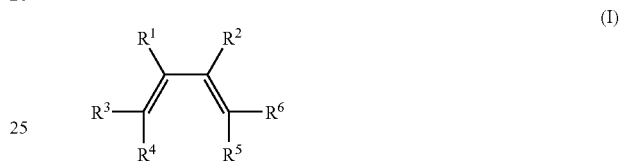

wherein $R^1$, $R^2$, $R^3$, $R^4$, $R^5$ and $R^6$ represent, simultaneously or independently from each other, a hydrogen atom or a $C_1$-$C_{12}$ alkyl or alkenyl group optionally substituted; one of $R^2$ or $R^6$ may also represent a $C_1$-$C_{12}$ alkoxy or acyloxy group optionally substituted; and $R^1$ and $R^3$, or $R^3$ and $R^4$, or $R^2$ and $R^6$, or $R^6$ and $R^5$, or $R^4$ and $R^5$, taken together, may form a $C_{2-16}$ alkanediyl or de-conjugated alkenediyl group, optionally substituted; into the corresponding alkene, of formula

wherein $R^1$ to $R^6$ have the same meaning as for the compound of formula (I), and wherein the isomer having the $R^1$ and $R^2$ groups in a cis configuration is predominant (i.e. the "cis"-alkene); said process being characterized in that it is carried out in the presence of at least one ruthenium catalyst or pre-catalyst of formula $$[Ru(L)(Diene)(L')_n]X \quad (III)$$

wherein L represents a $C_5$-$C_{25}$ derivative of cyclopentadienyl ligand (Cp), Diene represents a $C_4$-$C_{22}$ diene and X represents a non coordinated anion, n represent 2, 1 or 0 and L' represents a solvent; and at least an acidic additive of the type described further below, preferably in a total amount of about 0.1, or even 0.2, to 100 molar equivalents, relative to the compound (III).

Possible substituents of $R^1$ to $R^6$, when taken alone or together, are one or two groups which do no stop the reduction of the substrate by the catalyst. Non-limiting typical examples of such substituents are $OR^7$, $COR^7$, $OCOR^7$ or $COOR^8$, $R^7$ representing a hydrogen atom or a $C_1$-$C_{12}$ alkyl or alkenyl group, if one of the $R^1$ to $R^6$ is substituted with two geminal $OR^7$ groups, said two $R^7$ can be bound together to form a $C_2$-$C_4$ alkanediyl group, $R^8$ representing a $C_1$-$C_{12}$ alkyl or alkenyl group.

According to a particular embodiment of the invention, possible substituents of $R^1$ to $R^6$, when taken alone or together, are $OR^7$, $OCOR^7$ or $COOR^8$, $R^7$ representing a hydrogen atom or a $C_1$-$C_6$ alkyl or alkenyl group, if one of the $R^1$ to $R^6$ is substituted with two geminal $OR^7$ groups, said two $R^7$ can be bound together to form a $C_2$-$C_4$ alkanediyl group, $R^8$ representing a $C_1$-$C_6$ alkyl or alkenyl group. Said $R^7$ or $R^8$ can even be $C_1$-$C_6$ alkyl group.

When any of $R^1$, $R^2$, $R^3$, $R^4$, $R^5$ or $R^6$ represent an alkenyl group, then said group can be a de-conjugated or conjugated alkenyl group. It is understood that by "de-conjugated alkenyl" it is meant that the carbon carbon double bond of said group is not conjugated with the diene moiety, i.e. does not form a conjugated triene system.

It is understood that by "alkyl or de-conjugated alkenyl group" it is meant that said $R^1$ to $R^6$ can be in the form of, e.g., a linear, branched or (poly)cyclic group or can also be in the form of a mixture of said type of groups, e.g. a specific group may comprise a linear alkyl and a (poly)cyclic alkyl moiety, unless a specific limitation to only one type is mentioned.

Concerning compound (II), since it is an olefin, it can be obtained in the form of a mixture of two isomers, i.e. the one wherein the groups $R^1$ and $R^2$ are in a cis configuration ("cis"-alkene (II)) or wherein the groups $R^1$ and $R^2$ are in a trans configuration ("trans"-alkene (II'))

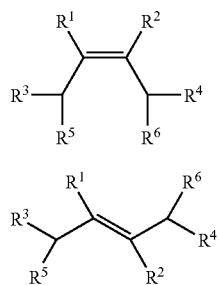

It is understood that according to the invention the alkene obtained is in the form of a mixture "cis"-alkene and "trans"-alkene, wherein the ratio "cis"-alkene/"trans"-alkene (cis/trans) is above 1. According to a particular embodiment, said ratio is above 4 or even above 10. In another particular embodiment, said cis/trans ratio can be above 19 or even above 30, and in some cases ratio of above 45 or more can be obtained. In any case the presence of the acidic additive in the prescribed concentration range allows to improve said ratio.

The substrate (I), due to the fact that it is a diene, can be in the form of a mixture of its three configuration isomers, i.e. the (Z,Z), (E,Z) and (E,E) isomers.

According to a further embodiment of the invention, the substrate is a diene comprising at least one ester or an alcohol functional group. Said diene can advantageously provide an unsaturated ester or alcohol useful in the pharmaceutical, agrochemical or perfumery industry as final product or as an intermediate. Particularly preferred substrate is a diene comprising at least one ester or an alcohol functional group, and said diene will provide an unsaturated ester or alcohol useful in the perfumery industry as final product or as an intermediate.

According to another embodiment of the invention, the substrate is a compound of formula (I) wherein $R^1$, $R^2$, $R^3$, $R^4$, $R^5$ and $R^6$ represent, simultaneously or independently from each other, a hydrogen atom or a $C_1$-$C_8$ alkyl or de-conjugated alkenyl group, optionally substituted; and $R^1$ and $R^3$, or $R^3$ and $R^4$, or $R^2$ and $R^6$, or $R^6$ and $R^5$, or $R^4$ and $R^5$, taken together, may form a $C_{3-10}$ alkanediyl or de-conjugated alkenediyl group, optionally substituted.

According to another embodiment of the invention, the substrate is a compound of formula (I) wherein $R^1$, $R^4$ and $R^5$ represent each a hydrogen atom; and $R^2$, $R^3$ and $R^6$ represent, simultaneously or independently from each other, a hydrogen atom or a $C_1$-$C_8$ alkyl or de-conjugated alkenyl group, optionally substituted.

Possible substituents of $R^1$ to $R^6$, when taken alone or together, are as described above.

Particular examples of substrate (I) are those of formula

wherein $R^a$ represents a linear, branched or cyclic $C_1$-$C_8$ alkyl or alkenyl group, preferably a linear or branched alkyl one; and
$R^b$ represents a $(CH_2)_m X$ group, m representing 0, 1, 2 or 3, X representing a CHO, OH, $OCOR^c$, $OR^c$ or $COOR^c$ group, $R^c$ being a $C_1$-$C_8$ alkyl or alkenyl group.

More specific examples are the compounds of formula (I') wherein $R^a$ represents a methyl, ethyl or propyl group, and $R^b$ a $(CH_2)_m X$ group, m representing 0, 1, or 2, X being as defined above. According to a particular embodiment the substrate can be sorbol, a $C_{1-8}$ alkyl sorbate, or a sorbol esters of $C_{1-8}$ carboxylates.

Furthermore, said substrate (I') can be essentially in the form of its (Z,Z) isomer (e.g. comprising at least 99% w/w of the isomer (Z,Z)).

Other particular examples of substrate (I) are those of formula

wherein $R^d$ and $R^e$ represent a hydrogen atom or a $C_1$-$C_8$ alkyl or alkenyle group, optionally substituted by a OH, $OCOR^f$, $OR^f$ or $COOR^f$ group, $R^f$ being a $C_1$-$C_8$ alkyl or alkenyl group, provided that $R^d$ and $R^e$ do not represent each a hydrogen atom.

More specific examples of the compounds of formula (I") can be the ocimene, myrcene, myrcenol or its $C_{1-8}$ carboxylates.

The process of the invention is characterized by the use, as catalyst or pre-catalyst (hereinafter referred to as complexes unless specified otherwise), of a ruthenium complex as described above.

According to a particular embodiment of the invention L' can be acyclic or cyclic non aromatic ketone or esters, such as acetone or methyl acetate. The ketone can be coordinated in its enolic form.

According to a particular embodiment of the invention, L can be a $C_6-C_{25}$ compound of formula

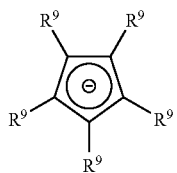

(IV)

wherein each $R^9$ represents, simultaneously or independently from each other, a hydrogen atom, a phenyl group optionally substituted, or a $C_1-C_{10}$ alkyl or alkenyl group optionally substituted; and
one or two of said groups $R^9$ can be a $CF_3$ group, a $OSiR^{11}_3$, $OCOR^{10}$, $COR^{10}$ or $COOR^{10}$ group, $R^{11}$ representing a $C_1-C_{11}$, or preferably a $C_1-C_6$, alkyl group, $R^{10}$ representing a $R^{11}$ or $CF_3$ group or a phenyl group optionally substituted; and
at least one $R^9$ is an alkyl group; two adjacent $R^9$ can be bound together to form a $C_2-C_{10}$ alkanediyl group.

Possible substituents of $R^9$, when representing a alkyl or alkenyl group, include one or two methyl, ethyl, methoxy or ethoxy groups. Possible substituents of $R^9$, when representing a phenyl group, or of $R^{10}$, include one or two methyl, ethyl, methoxy, ethoxy or nitro groups or $CF_3$, F, Cl, Br groups.

According to an embodiment of the invention, L can be a $C_6-C_{20}$ compound of formula (IV) wherein
each $R^9$ represents, simultaneously or independently from each other, a hydrogen atom, a $C_1-C_{10}$ alkyl or alkenyl group; and
one or two of said groups $R^9$ can be a $OSiR^{11}_3$, $OCOR^{10}$, $COR^{10}$ or $COOR^{10}$ group, $R^{11}$ representing a $C_1-C_4$ alkyl group, $R^{10}$ representing a $R^{11}$ or $CF_3$ group or a phenyl group optionally substituted, as described above; and
at least one $R^9$ is an alkyl group.

According to an embodiment of the invention, L can be a $C_6-C_{20}$ compound of formula (IV) wherein
each $R^9$ represents, simultaneously or independently from each other, a hydrogen atom, a $C_1-C_{10}$ alkyl or alkenyl group; and
one or two of said groups $R^9$ can be a $OSiR^{11}_3$, $R^{11}$ representing a $C_1-C_4$ alkyl group; and at least one $R^9$ is an alkyl group.

According to an embodiment of the invention, four $R^9$ represent, simultaneously or independently from each other, a hydrogen atom or a $C_1-C_4$ alkyl group (such as methyl or ethyl) and one $R^9$ represents $OSiR^{11}_3$, $R^{11}$ representing a $C_1-C_4$ alkyl group (such as methyl or ethyl), and at least one $R^9$ is an alkyl group.

According to an embodiment of the invention, two $R^9$ represent, simultaneously or independently from each other, a hydrogen atom or a $C_1-C_4$ alkyl group (such as methyl or ethyl) and the three other $R^9$ represent, simultaneously or independently, a $C_1-C_4$ alkyl groups (such as methyl or ethyl).

According to another particular embodiment of the invention one $R^9$ represents a hydrogen atom or a methyl or ethyl group and the other $R^9$ represent a methyl or ethyl group. In particular compound (IV) can be 1,2,3,4,5-pentamethyl-cyclopentadienyl (i.e. Cp* or $C_5Me_5$), 1-ethyl-2,3,4,5-tetramethyl-cyclopentadienyl (i.e. $C_5EtMe_4$), 1,2-diethyl-3,4,5-trimethyl-cyclopentadienyl (i.e. $C_5(1,2-Et_2)Me_3$) or 1,2,3,4,5-pentaethyl-cyclopentadienyl ($C_5Et_5$).

The cyclopentadiene precursor CpH of the cyclopentadienyl ligand Cp (L) mentioned above can be obtained by applying standard general methods which are well known in the state of the art and by the person skilled in the art (see for example WO 2006/051503). Some of said ligands are even commercially available.

The Diene can be a $C_4-C_{22}$ non-aromatic hydrocarbon group comprising two carbon-carbon double bonds, said carbon-carbon double bonds can be conjugated or non-conjugated. Said Diene can be in particular a linear, branched or cyclic $C_5-C_{12}$ hydrocarbon diene optionally substituted by the same substituents as described for $R^1$ to $R^6$ herein above. Furthermore, it is also understood that said Diene can be the substrate itself or a different compound.

According to a particular embodiment the Diene is preferably a conjugated or non conjugated cyclic $C_6-C_{12}$ alkadiene, and in particular one of the cyclooctadienes (COD).

As typical, and non-limiting, examples of Diene, one may cite the following: cycloocta-1,5-diene, cycloocta-1,4-diene, cycloocta-1,3-diene, NBD (norbornadiene), hepta-1,4-diene, pentadiene, 2,4-dimethylpentadiene, 2,3-dimethylpentadiene, 2,3,4-trimethylpentadiene, 2,4-di(tert-butyl)-pentadiene or yet 2,4-dimethyl-1-oxapentadiene, butadiene, hexa-1,5-diene, or a compound of formula (I') or (I'') as mentioned above.

Particular examples of the non-coordinated anion X are $ClO_4^-$, $R^{12}SO_3^-$, wherein $R^{12}$ is a chlorine of fluoride atom or an $C_1-C_8$ fluoroalkyl or fluoroaryl group, $BF_4^-$, $PF_6^-$, $SbCl_6^-$, $SbF_6^-$, or $BR^{13}_4^-$, wherein $R^{13}$ is a phenyl group optionally substituted by one to five groups such as halide atoms or methyl or $CF_3$ groups.

According to a preferred embodiment of the invention, the anion is $BF_4^-$, $PF_6^-$, $C_6F_5SO_3^-$, $BPh_4^-$, $CF_3SO_3^-$ or yet $B[3,5-(CF_3)_2C_6H_4]_4^-$, even more preferably $BF_4^-$.

As examples of the complex (III) one may cite the following: $[Ru(C_5Me_5)(1,3-COD)]BF_4$, $[Ru(C_5Et_5)(1,3-COD)]BF_4$, $[Ru(C_5Me_4H)(1,3-COD)]BF_4$, $[Ru(C_5(1,2-{}^iPr_2)Me_3)(1,3-COD)]BF_4$, $[Ru(C_5(1,2,4-{}^tBu_3)H_2)(1,3-COD)]BF_4$, $[Ru(C_5Me_4{}^tBu)(1,3-COD)]BF_4$, $[Ru(C_5Me_4(OSiMe_3))(1,3-COD)]BF_4$, $[Ru(C_5(1,2-Et_2)Me_3)(1,3-COD)]BF_4$, $[Ru(C_5Me_5)(1,3-COD)]PF_6$, $[Ru(C_5Me_5)(1,3-COD)]SbF_6$, $[Ru(C_5Me_5)(1,3-COD)]ClO_4$, $[Ru(C_5Me_5)(1,3-COD)]CF_3SO_3$, $[Ru(C_5Me_5)(NBD)(C_3H_6O)]BF_4$, $[Ru(C_5Me_5)(1,5-hexadiene)(C_3H_6O)]BF_4$, or $[Ru(C_5Me_5)(dimethylbutadiene)(C_3H_6O)]BF_4$.

In a general way, the complexes of formula (III) can be prepared and isolated prior to their use in the process according to some methods described in the literature for example by P. J. Fagan et al. (*Organometallics*, 1990, 9, pg 1843-1852), F. Bouachir et al. (*Organometallics*, 1991, 10, pg 455-462) or P. Alvarez et al. (*Organometallics*, 1991, 20, pg 3762-3771), the one chosen depending on the nature of cyclopentadienyl and diene ligands and also of the non-coordinating anion.

It is also understood that the complex of formula (III) can also be obtained in situ from complexes which have a similar formula and are cationic or anionic according to the standard knowledge of a person skilled in the art. For example, reaction can be run using [Ru(Cp*)(COD)Y] (Y being F, Cl, Br or I and method for preparation having been described by P. J. Fagan et al. in *Organometallics*, 1990, 9, pg 1843-1852) as precursors in the presence of the substrate and silver or tallium salts).

From the present invention, it is preferably excluded the case wherein the substrate is sorbol and the catalysts is [(Cp*)Ru(COD)]X.

Many of the above-mentioned complexes of formula (III) are new and therefore represent also another aspect of the present invention.

In particular said new complexes (III) can be the ones wherein L is a $C_6$-$C_{25}$ compound of formula

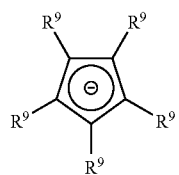

(IV)

wherein each $R^9$ represents, simultaneously or independently from each other, a hydrogen atom, a phenyl group optionally substituted, or a $C_1$-$C_{10}$ alkyl or alkenyl group optionally substituted; and
one or two of said groups $R^9$ is a $OSiR^{11}_3$ or $OCOR^{10}$ group, $R^{11}$ representing a $C_1$-$C_6$ alkyl group, $R^{10}$ representing a $R^{11}$ or $CF_3$ group or a phenyl group optionally substituted; and at least one $R^9$ is an alkyl group; two adjacent $R^9$ can be bound together to form a $C_2$-$C_{10}$ alkanediyl group.

Possible substituents of $R^9$, when representing a alkyl or alkenyl group, include one or two methyl, ethyl, methoxy or ethoxy groups. Possible substituents of $R^9$, when representing a phenyl group, or of $R^{10}$, include one or two methyl, ethyl, methoxy, ethoxy or nitro groups or $CF_3$, F, Cl, Br groups.

According to an embodiment of the invention, four $R^9$ represent, simultaneously or independently from each other, a hydrogen atom or a $C_1$-$C_4$ alkyl group (such as methyl or ethyl) and one $R^9$ represents $OSiR^{11}_3$, $R^{11}$ representing a $C_1$-$C_4$ alkyl group (such as methyl or ethyl), and at least one $R^9$ is an alkyl group.

To carry out the processes of the invention, it is required also to use at least an acidic additive. By "acidic additive" it is meant a compound capable of providing at least one proton to the catalytic cycle. Said acidic additive is preferably an organic or inorganic compound having a $pK_a$ comprised between 0.8 and 7, but in the case of phenols or boron derivatives said $pK_a$ can range up to 10.

Furthermore, said acidic additive can be selected from the group consisting of:
compound of formula $R^{14}_{(3-x)}MO(OH)_x$, wherein $R^{14}$ is a $R^{14'}$ or $R^{14'}$ group wherein $R^{14'}$ is a $C_1$-$C_{10}$ group, M is P or As and x is 1 or 2;
a boron derivative of formula $R^{14}B(OH)_2$, wherein $R^{14}$ is as defined above; and
phenol or a phenol substituted by up to three $C_1$-$C_4$ alkyl, alkoxy or carboxylic groups, nitro groups or halogen atoms;
a $C_1$-$C_{12}$ mono-carboxylic non-amino acid;
a HOOCCH=CHCOOH di-acid, or the tetronic acid.

By "mono-carboxylic non-amino acid" it is meant here a mono-carboxylic acid which is not substituted by a primary, secondary or tertiary amino group or heteroaromatic nitrogen derivatives.

According to a particular embodiment, said $R^{14}_{(3-x)}MO(OH)_x$ acids can be a derivative wherein $R^{14}$ is a $C_1$-$C_8$ alkyl or alkoxyl group or a $C_6$-$C_8$ phenyl or phenoxyl group optionally substituted, M is P or As and x is 1 or 2.

Similarly said $R^{14}B(OH)_2$ acids can be those wherein $R^{14}$ is a $C_1$-$C_8$ alkyl or alkoxyl group or a $C_1$-$C_8$ phenyl or phenoxyl group optionally substituted.

According to another embodiment of the invention, said acid can be the phenol or a phenol substituted by one $C_1$-$C_4$ alkyl, alkoxy or carboxylic group, a nitro group or a halogen atom.

Furthermore, according to an other particular embodiment of the invention, said acidic additive can be a mono-carboxylic acid of formula $R^{15}COOH$, wherein $R^{15}$ represents a $C_1$-$C_{12}$ hydrocarbon group or a $C_1$-$C_{12}$ halogenated or per-halogenated hydrocarbon group, optionally substituted by one alcohol group or one or two ether or ester groups. According to a further embodiment, said carboxylic acid is advantageously selected from the group consisting of:
a carboxylic acid of formula $R^{15}COOH$, wherein $R^{15}$ represents
a halogenated or per-halogenated $C_1$-$C_8$ hydrocarbon group;
a $R^{16}CH(OR^{16})$ group, $R^{16}$ being a hydrogen atom or a $C_1$-$C_6$ hydrocarbon group;
a $C_1$-$C_{12}$ hydrocarbon group, optionally substituted by one or two ether or ester groups, the optional substituent being by one, two or three $C_1$-$C_4$ alkyl, alkoxy or carboxylic groups, or nitro groups or halogen atoms.

One can cite, as non-limiting examples, of said acidic additive the following: $(BuO)_2PO(OH)$, $(^tBuO)_2PO(OH)$, $(PhO)_2PO(OH)$, $(PhCH_2O)_2PO(OH)$, $^tBuPO(OH)_2$, $Ph_2PO(OH)$, $PhPO(OH)_2$, $PhAsO(OH)_2$, $(Me)_2AsO(OH)$, $CF_3COOH$, $HCF_2COOH$, maleic or fumaric acid, glycolic acid, pyruvic acid, sorbic, acetic or oleic acid, tetronic acid, $C_6H_{13}B(OH)_2$, $PhB(OH)_2$, p-OMe-benzoic, benzoic or p-(COOMe)-benzoic acid, phenol, 3,5-dimethoxy-phenol or 2-methoxy-phenol. Of course, other suitable acidic additives responding to the above description can be used.

According to another embodiment of the invention, said acidic additives can be selected from the group consisting of:
a compound of formula $R^{14}_2MO(OH)$ or $R^{14}MO(OH)_2$, wherein $R^{14}$ is a $C_1$-$C_6$ alkyl or alkoxyl group or a $C_6$-$C_8$ phenyl or phenoxyl and M is P or As; and
maleic or glycolic acid and an halogenated or per-halogenated $C_1$-$C_7$ mono-carboxylic acid.

As previously mentioned, the processes of the invention consist in the hydrogenation of a substrate using a ruthenium complex and an acidic additive. A typical process implies the mixture of the substrate with the ruthenium complex, at least one acidic additive and optionally a solvent, and then treating such a mixture with molecular hydrogen at a chosen pressure and temperature.

The complexes of the invention, an essential parameter of the process, can be added to the reaction medium in a large range of concentrations. As non-limiting examples, one can cite as complex concentration values those ranging from 0.01 mol % to 5 mol %, the molar percentage being relative to the amount of substrate. Preferably, the complex concentration will be comprised between 0.03 mol % to 2 mol %. It goes without saying that the optimum concentration of complex will depend, as the person skilled in the art knows, on the nature of the latter, on the nature of the substrate, on the nature of the solvent and on the pressure of $H_2$ used during the process, as well as the desired time of reaction.

Useful quantities of acidic additive, added to the reaction mixture, may be comprised in a relatively large range. Apart from the one above cited, one can cite, as non-limiting examples, total amounts ranging between 0.5 to 50 molar equivalents, relative to the complex, preferably 0.8 to 20, and even more preferably between about 2 and about 10 molar equivalents.

The hydrogenation reaction can be carried out in the presence or absence of a solvent. When a solvent is required or used for practical reasons, then any solvent current in hydrogenation reactions can be used for the purposes of the invention. Non-limiting examples include non-aromatic solvents such as $C_1$-$C_{12}$ non aromatic ketones, esters, alkanes ethers, chlorinated alkanes and alcohols or mixtures thereof. According to an embodiment of the invention, the solvent is advantageously selected amongst the $C_1$-$C_{12}$ alkyl ketones, esters, ethers or chlorinated alkanes. In particular and as non-limiting examples one may cite the following: acetone ethyl acetate, MTBE, THF, iso-propyl acetate, $Et_2O$, dichloromethane, 1,2-dichloethane, EtoH, MeOH, pentane, hexane. The choice of the solvent can be done as a function of the nature of the complex and the person skilled in the art is well able to select the solvent most convenient in each case to optimize the hydrogenation reaction.

In the hydrogenation process of the invention, the reaction can be carried out at a $H_2$ pressure comprised between $10^5$ Pa and $80 \times 10^5$ Pa (1 to 80 bars) or even more if desired. Again, a person skilled in the art is well able to adjust the pressure as a function of the catalyst load and of the dilution of the substrate in the solvent. As examples, one can cite typical pressures of 1 to $30 \times 10^5$ Pa (1 to 30 bar).

The temperature at which the hydrogenation can be carried out is comprised between 0° C. and 120° C., more preferably in the range of between 40° C. and 100° C. Of course, a person skilled in the art is also able to select the preferred temperature as a function of the melting and boiling point of the starting and final products as well as the desired time of reaction or conversion.

EXAMPLES

The invention will now be described in further detail by way of the following examples, wherein the temperatures are indicated in degrees centigrade and the abbreviations have the usual meaning in the art.

All the procedures described hereafter have been carried out under an inert atmosphere unless stated otherwise. Hydrogenations were carried out in open glass tubes placed inside a stainless steel autoclave. $H_2$ gas (99.99990%) was used as received. All substrates and solvents were distilled from appropriate drying agents under Ar. NMR spectra were recorded on a Bruker AM-400 (400 MHz) spectrometer and normally measured at 300 K, in $CD_2Cl_2$ unless indicated otherwise. Chemical shifts are listed in ppm and coupling constant J are in Hz.

Example 1

A) Synthesis of Cyclopentadienes

Cyclopentadienes were synthesized starting from substituted cyclopentenones prepared according to procedure previously described in patent WO 2006051503.

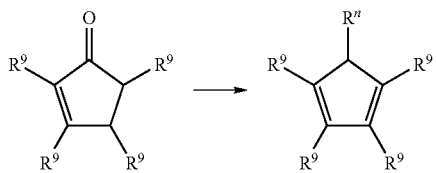

Cyclopentadienes were generally obtained in high molar yields (>80%) and purity (>95%).

$R''$ is an Alkyl or Alkenyl Group

A solution of cyclopentenone (1 equivalents) in THF (1.6 M) was added at 0° C. under inert atmosphere to a solution of $R''MgCl$ (1.2 equivalents). Reaction mixture was then allowed to warm to room temperature and stirred for 3 hours. Acetic acid 10% was then added to the reaction mixture and the organic phase was extracted with $Et_2O$. HCl (20% in water) was added to the organic phase and allowed to stir for 30 minutes. The organic phase was then neutralized with $NaHCO_3$ (5% in water). Washing with water, drying and evaporation of solvent gave a crude product, which was purified by distillation.

$R''$=H

Cyclopentenenones were reduced by $NaBH_4$ (0.5 equivalents) in EtOH under inert atmosphere. After work-up, the crude products were purified by fractionated distillation.

$R''$=Alkoxy or Siloxy

A solution of $Li(NiPr)_2$ (1.2 equivalents) in THF (2M) was added to a solution of cyclopentanone (1 equivalent) in THF (0.1 M) at −78° C. After 1 hour stirring the alkyl halide $R''$-halide or the siloxy halide $(R^{11})_3Si$-halide (1.5 equivalents) was added to the reaction mixture.

Reaction mixture was then allowed to warm to room temperature and stirred for 5 hours. Reaction mixture was evaporated to dryness and n-hexane was added. The solid salts were eliminated by filtration and the solution was then evaporated to dryness. The crude product was purified by distillation.

Ligand $C_5(1,2,4-^tBu_3)H_2$ was synthesized according to the literature (E. V. Dehmlow, C. Bollmann, *Z. Naturforsch.*, 1993, 48b, 457-460).

B) Catalyst Synthesis

Ruthenium catalysts were synthesized according to three different ways depending on the nature of cyclopentadienyle and diene ligands but also of the counter-ion. All the solvent used were dried and stored under inert atmosphere.

Method 1:

[Ru(L)(1,3-COD)]$BF_4$ complexes with L being a cyclopentadienyl ligand bearing no aromatic groups were obtained in two steps starting from [Ru(COD)(COT)], via [(CODyl)$_2$RuH][$BF_4$], both obtained according to a procedure previously described by F. Bouachir, B. Chaudret, F. Dahan, F. Agbossou, I. Tkatchenko, *Organometallics*, 1991, 10, 455-462.

To [Ru(CODyl)$_2$H]$BF_4$ in solution in $CH_2Cl_2$ (0.05 M) under inert atmosphere was added a stoechiometric amount of the desired substituted cyclopentadiene derivative L (1 equivalent/Ru) and reaction mixture was stirred at room temperature for 16 hours. It was then concentrated to dryness. [(L)Ru(1,3-COD)][$BF_4$] complexes were crystallized from a $CH_2Cl_2/Et_2O$ mixture. It was obtained in more than 80% molar yield after filtration and drying under vacuum.

[Ru($C_5Me_5$)(1,3-COD)]$BF_4$:
$^1$H NMR (233° K): 6.44 (t, J=6.8, 1H); 4.89 (m, 2H); 3.38 (m, 2H); 1.89 (m, 2H); 1.85 (s, 15H); 1.50 (m, 2H); 1.41 (m, 1H); 0.35 (q, J=13.6, 1H); −10.41 (s broad, 1H).

$^{13}$C NMR (233° K): 106.36, 98.30, 83.88, 40.94, 21.92, 18.89, 10.27.

[Ru($C_5Et_5$)(1,3-COD)]$BF_4$:
$^1$H NMR (233K): 6.41 (t, J=6.8, 1H); 4.87 (m, 2H); 3.36 (m, 2H); 2.20 (q, J=7.5, 10H); 1.91 (m, 2H); 1.47 (m, 2H); 1.40 (m, 1H); 1.22 (t, J=7.52, 15H); 0.37 (m, 1H); −10.48 (s broad, 1H).

$^{13}$C NMR (233K): 102.61, 91.20, 77.49, 48.92, 29.35, 21.98, 10.01.

[Ru($C_5Me_4H$)(1,3-COD)]$BF_4$:
$^1$H NMR (233K): 6.46 (t, J=6.8, 1H); 5.37 (s, 2H); 4.97 (m, 2H); 3.43 (m, 2H); 1.87 (dt, J=4.12, 15.68, 2H); 1.77 (s, 6H); 1.74 (s, 6H); 1.50 (m, 2H); 1.37 (dt, J=3.4, 15.0, 1H)

$^{13}$C NMR (233K): 106.59, 100.01, 99.30, 83.79, 82.64, 40.76, 21.93, 18.88, 11.56, 9.76.

[Ru($C_5Me_4{}^tBu$)(1,3-COD)]$BF_4$:
$^1$H NMR (233K): 6.51 (t, J=6.8, 1H); 4.93 (m, 2H); 3.41 (m, 2H); 1.96 (m, 2H); 1.91 (s, 6H); 1.66 (s, 6H); 1.55 (m, 2H); 1.51 (s, 9H); 1.44 (m, 1H); 0.48 (m, 1H); −10.35 (s broad, 1H).

$^{13}$C NMR (233K): 108.79, 106.83, 99.73, 99.21, 84.21, 41.77, 33.84, 32.47, 22.31, 18.91, 13.18, 9.97.

[Ru(C$_5$(1,2-$^i$Pr$_2$)Me$_3$)(1,3-COD)]BF$_4$:
$^1$H NMR (233K): 6.54 (t, J=6.8, 1H); 4.97 (m, 2H); 3.51 (m, 2H); 2.88 (m, 2H) 1.96 (dt, J=3.4, 15.7, 2H); 1.83 (s, 6H); 1.54 (m, 2H); 1.51 (s, 3H); 1.45 (m, 1H); 1.36 (d, J=6.8, 6H); 1.32 (d, J=7.5, 6H); 0.44 (qt, J=3.4, 14.3, 1H); −10.36 (s broad, 1H).
$^{13}$C NMR (233K): 102.61, 91.20, 95.71, 77.49, 48.92, 29.35, 21.98, 10.01.

[Ru(C$_5$Me$_4$(Me$_3$SiO))(1,3-COD)]BF$_4$:
$^1$H NMR (233K): 6.23 (t, J=6.8, 1H); 4.74 (m, 2H); 3.34 (m, 2H); 2.03 (s, 6H); 1.47 (s, 6H); 1.51 (m, 2H); 1.35 (m, 1H); 0.38 (m, 1H); 0.03 (s, 9H); 9.19 (s broad, 1H).
$^{13}$C NMR (233K): 138.96, 106.79, 92.85, 90.86, 86.49, 83.59, 39.76, 22.25, 19.35, 9.26, 9.18, 0.00.

[Ru(C$_5$(1,2,4-$^t$Bu$_3$)H$_2$) (1,3-COD)]BF$_4$:
$^1$H NMR (233K): 7.02 (t, J=6.8, 1H); 5.51 (m, 2H); 5.22 (s, 2H); 3.97 (m, 2H); 2.01 (m, 2H); 1.54 (m, 2H); 1.49 (m, 1H); 1.35 (s, 18H); 1.19 (s, 9H); 0.48 (m, 1H); 10.89 (s broad, 1H).
$^{13}$C NMR (233K): 114.06, 112.76, 106.98, 83.66, 81.94, 36.93, 33.31, 31.35, 31.21, 30.78, 21.58, 18.60.

Method 2:

[Ru(L)(diene)]X complexes with cyclopentadienyl ligand bearing no aromatic groups could also be obtained according to a multi-steps procedure previously described by] P. J. Fagan, M. D. Ward, J. C. Calabrese, *J. Am. Chem., Soc.,* 1989, 111, 1698-1719 or by P. J. Fagan, W. S. Mahoney, j. C. Calabrese, I. D. Williams, *Organometallics,* 1990, 9, 1843-1852.

[Ru(L)Cl$_2$] was first obtained reacting RuCl$_3$.xH$_2$0 in EtOH (0.25 M) with an excess of the desired substituted cyclopentadiene derivative L (2.5 equivalents/Ru). The reaction mixture was heated to reflux under inert atmosphere for 3 hours and then cooled down to room temperature. Desired product was recovered by filtration. It was obtained in more than 70% molar yield after washings with EtOH and drying under vacuum.

[Ru(L)Cl]$_4$ was then obtained by reaction at room temperature under inert atmosphere of a [Ru(L)Cl$_2$] suspension in THF (0.6 M) with 1 equivalent/Ru of a 1 M lithium triethylborohydride solution in THF. After stirring at room temperature for 1 hour, reaction mixture was filtered under inert atmosphere. Recovered product was obtained in more than 75% molar yield after washing with THF and drying under vacuum.

[Ru(L)(diene)Cl] was obtained by reaction at room temperature under inert atmosphere of [Ru(L)Cl]$_4$ in solution in THF (0.05 M) with a slight excess of the desired diene (1.5 equivalents/Ru). After stirring for 1 hour, reaction mixture was filtered under inert atmosphere and the retrieved solution was concentrated to dryness. The obtained residue was precipitated by trituration in pentane and solid product was retrieved by filtration under inert atmosphere. It was obtained in more than 75% molar yield after washing with pentane and drying under vacuum.

[Ru(L)(diene)]X was obtained by reaction at room temperature under inert atmosphere of [Ru(L)(diene)Cl] in solution in acetone (0.25 M) with stoechiometric amount (1 equivalents/Ru) of AgX. After stirring at room temperature for 1 hour, reaction mixture was filtered under inert atmosphere and the retrieved solution was concentrated to dryness. [Ru(L)(diene)]X was crystallized from a CH$_2$Cl$_2$/Et$_2$O mixture. It was obtained in more than 75% molar yield after filtration drying under vacuum. It is worth noticing that product was sometimes obtained as the acetone adduct depending mainly on the nature of the diene, acetone being then coordinated to the ruthenium centre as the ketone or enol form (observed by IR spectroscopy).

[Ru(C$_5$Me$_5$)(NBD)]BF$_4$:
$^1$H NMR (298K); 4.61 (m, 2H); 4.52 (m, 2H); 4.26 (m, 2H); 3.86 (m, 2H); 1.55 (s, 15H).
$^{13}$C NMR (298K): 94.95, 78.43, 65.53, 64.54, 51.99, 9.48.

[Ru(C$_5$Me$_5$)(dimethylbutadiene)]BF$_4$:
$^1$H NMR (298K); 4.01 (s, 4H); 1.96 (s, 6H); 1.55 (s, 15H).
$^{13}$C NMR (298K): 108.63, 97.33, 59.22, 32.25, 19.14, 9.26.

[Ru(C$_5$Me$_5$)(2,4-hexadienylacetate)]BF$_4$:
$^1$H NMR (298K): 6.32 (dq, J=6.84, 15.17, 1H); 5.85 (m, 1H); 5.36 (m, 1H); 4.43 (d, J=6.08, 1H); 4.29 (t, J=10.6, 1H); 3.08 (d, J=10.6, 1H), 1.94 (s, 3H), 1.63 (dd, J=1.52, 6.84, 3H), 1.56 (s, 15H).
$^{13}$C NMR (298K): 193.99, 139.07, 129.67, 106.23, 102.23, 91.88, 66.31, 25.52, 19.84, 9.38.

[Ru(C$_5$Me$_5$)(1,3-COD)]CF$_3$SO$_3$:
$^1$H NMR (233K): 6.45 (t, J=6.8, 1H); 4.91 (m, 2H); 3.39 (m, 2H); 1.90 (m, 2H); 1.85 (s, 15H); 1.51 (m, 2H); 1.40 (m, 1H); 0.37 (qt, J=3.4, 13.64, 1H); 10.40 (s broad, 1H).
$^{13}$C NMR (233K): 106.59, 98.42, 84.29, 41.29, 22.01, 18.92, 10.08.

[Ru(C$_5$Me$_5$)(1,3-COD)]PF$_6$:
$^1$H NMR (233K): 6.39 (t, J=6.8 Hz, 1H); 4.86 (m, 2H); 3.37 (m, 2H); 1.91 (m, 2H); 1.84 (s, 15H); 1.51 (m, 2H); 1.41 (m, 1H); 0.37 (qt, J=3.4, 14.4, 1H); −10.41 (s broad, 1H).
$^{13}$C NMR (233K): 106.49, 98.46, 84.20, 41.32, 21.99, 18.90, 10.04.

[Ru(C$_5$Me$_5$)(1,3-COD)]ClO$_4$:
$^1$H NMR (233K): 6.45 (t, J=6.8, 1H); 4.91 (m, 2H); 3.39 (m, 2H); 1.90 (m, 2H); 1.86 (s, 15H); 1.53 (m, 2H); 1.41 (m, 1H); 0.38 (qt, J=3.4, 14.4, 1H); −10.38 (s broad, 1H).
$^{13}$C NMR (233K): 106.58, 98.43, 84.28, 41.31, 22.01, 18.94, 10.11.

[Ru(C$_5$Me$_5$)(1,3-COD)]SbF$_6$:
$^1$H NMR (233K): 6.38 (t, J=6.8, 1H); 4.85 (m, 2H); 3.37 (m, 2H); 1.91 (m, 2H); 1.84 (s, 15H); 1.51 (m, 2H); 1.42 (m, 1H); 0.38 (qt, J=3.4, 14.4, 1H); −10.39 (s broad, 1H).
$^{13}$C NMR (233K): 106.49, 98.49, 84.22, 41.37, 22.01, 18.91, 10.04.

Method 3:

[Ru(L)(COD)]BF$_4$ complexes with cyclopentadienyl ligands L bearing aromatic groups were obtained according to a multi-step procedure previously described by P. Alvarez, J. Gimeno, E. Lastra, S. Garcia-Granda, J. F. Van der Maelen, M. Bassetti, *Organometallics,* 2001, 20, 3762-3771.

[Ru(L)(diene)Cl] was obtained by reaction at room temperature under inert atmosphere of [Ru(diene)Cl2] in suspension in THF (0.05) with a stoechiometric amount (1 equivalents/Ru) of a freshly prepared solution of L sodium salt in THF. After stirring for 1 hour at room temperature, a slight excess (1.2 equivalents/Ru) of HCl in solution in Et$_2$O (2 M) was added to reaction mixture that was stirred at this temperature for an additional hour. It was then filtered under inert atmosphere and the retrieved solution was concentrated to dryness. The obtained residue was precipitated by trituration in pentane and solid product was retrieved by filtration under inert atmosphere. It was obtained in more than 70% molar yield after washing with pentane and drying under vacuum.

[Ru(L)(diene)]] was obtained by reaction at room temperature under inert atmosphere of [Ru(L)(diene)Cl] in solution in acetone (0.25 M) with stoechiometric amount (1 equivalent/Ru) of AgX. After stirring at room temperature for 1 hour, reaction mixture was filtered under inert atmosphere and the retrieved solution was concentrated to dryness. [Ru(L)(diene)]X was crystallized from a $CH_2Cl_2/Et_2O$ mixture. It was obtained in more than 75% molar yield after filtration drying under vacuum. It is worth noticing that product was sometimes obtained as the acetone adduct depending mainly on the nature of the diene, acetone being then coordinated to the ruthenium centre as the ketone or enol form.

Example 2

Hydrogenation Processes According to the Invention

Typical Hydrogenation Reaction Procedure

Substrate, solvent, [Ru(L)(Diene)]X and the acidic additive according to the invention were loaded altogether under inert atmosphere an autoclave and the mixture was purged at room temperature with nitrogen (2 bars, 3 times) and then hydrogen (2 bars, 3 times) under stirring. The autoclave was then pressurized to the desired hydrogen pressure and heated at the desired temperature. The reaction was followed by hydrogen absorption monitoring and/or GC analysis sampling. The ruthenium catalyst was easily removed by distillation on residues and product isomers mixture was usually recovered in more than 90% molar yield.

The results obtained are summarized in the following tables.

TABLE 1 influence of the acidic additive and of its presence on hydrogenation selectivity reaction type:

Myrcene $[Ru(C_5Me_5)(1,3\text{-}COD)]BF_4$ (0.1 mol. %)
acidic additive (0.5 mol. %)
$H_2$ (5 bars), 70° C., acetone (50 wt. %)

complete conversion

| Acidic additive | 1,4-Selectivity | Ratio "cis"-alkene/"trans"-alkene |
|---|---|---|
| none | >98% | 52/48 |
| $(Ph)_2P(O)(OH)$ | >98% | 82/18 |
| maleic acid | >98% | 95/5 |
| $(BuO)_2P(O)OH$ | >98% | 87/13 |
| $Me_2As(O)OH$ | >98% | 74/26 |
| 2-methoxyphenol | >98% | 65/35 |
| Sorbic acid | >98% | 60/40 |
| Trifluoroacetic acid | >95% | 80/20 |
| Glycolic acid | >98% | 85/15 |

TABLE 2 influence of the acidic additive and of its presence on hydrogenation selectivity reaction type:

Myrcenyl acetate $[Ru(C_5Me_5)(1,3\text{-}COD)]BF_4$ (0.1 mol. %)
acidic additive (0.5 mol. %)
$H_2$ (5 bars), 70° C., acetone (50 wt. %)

complete conversion

| Acidic additive | 1,4-Selectivity | Ratio "cis"-alkene/"trans"-alkene |
|---|---|---|
| none | >98% | 45/55 |
| $(C_6H_{13})B(OH)_2$ | >98% | 52/48 |
| sorbic acid | >98% | 55/45 |
| $(Ph)_2P(O)(OH)$ | >98% | 82/18 |
| maleic acid | >98% | 96/4 |
| $(BuO)_2P(O)OH$ | >98% | 85/15 |
| 2-methoxyphenol | >98% | 60/40 |
| Trifluoroacetic acid | >95% | 75/25 |
| $Me_2As(O)OH$ | >98% | 70/30 |
| Glycolic acid | >98% | 80/20 |

TABLE 3 influence of the acidic additive and of its presence on hydrogenation selectivity reaction type:

cis-ocimene $[Ru(C_5Me_5)(1,3\text{-}COD)]BF_4$ (0.1 mol. %)
acidic additive (0.5 mol. %)
$H_2$ (5 bars), 70° C., acetone (50 wt. %)

complete conversion

| Acidic additive | 1,4-Selectivity | Ratio "cis"-alkene/"trans"-alkene |
|---|---|---|
| none | >98% | 3/97 |
| $(Ph)_2P(O)(OH)$ | >98% | 83/17 |
| $(BuO)_2P(O)OH$ | >98% | 88/12 |
| Maleic acid | >98% | 93/7 |
| Trifluoroacetic acid | >90% | 80/20 |
| Glycolic acid | >98% | 85/15 |

TABLE 4 influence of the acidic additive and of its presence on hydrogenation selectivity reaction type:

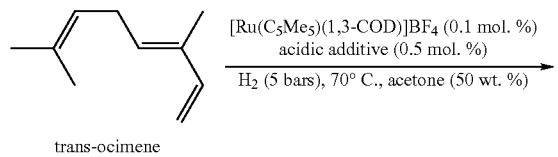

trans-ocimene

[Ru(C$_5$Me$_5$)(1,3-COD)]BF$_4$ (0.1 mol. %)
acidic additive (0.5 mol. %)
H$_2$ (5 bars), 70° C., acetone (50 wt. %)

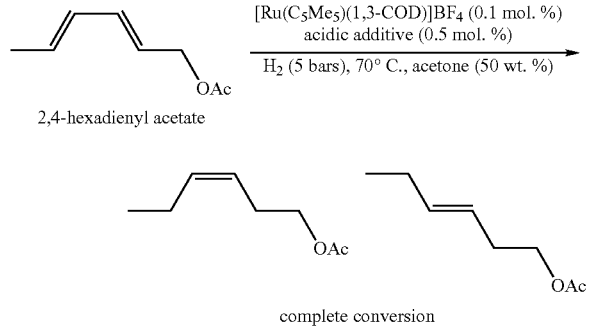

complete conversion

| Acidic additive | 1,4-Selectivity | Ratio "cis"-alkene/"trans"-alkene |
|---|---|---|
| none | >98% | 83/17 |
| maleic acid | >98% | 95/5 |
| (Ph)$_2$P(O)(OH) | >98% | 94/6 |
| (BuO)$_2$P(O)OH | >98% | 90/10 |

TABLE 5 influence of the acidic additive and of its presence on hydrogenation selectivity reaction type:

2,4-hexadienyl acetate

[Ru(C$_5$Me$_5$)(1,3-COD)]BF$_4$ (0.1 mol. %)
acidic additive (0.5 mol. %)
H$_2$ (5 bars), 70° C., acetone (50 wt. %)

complete conversion

| Acidic additive | 1,4-Selectivity | Ratio "cis"-alkene/"trans"-alkene |
|---|---|---|
| none | >98% | 88/12 |
| (Ph)$_2$P(O)(OH) | >98% | 96/4 |
| (BuO)$_2$P(O)OH | >98% | 95/5 |
| maleic acid | >98% | 98/2 |
| 2-methoxyphenol | >98% | 90/10 |
| Glycolic acid | >98% | 93/17 |

TABLE 6 influence of the acidic additive and of its presence on hydrogenation selectivity influence of the Diene reaction type:

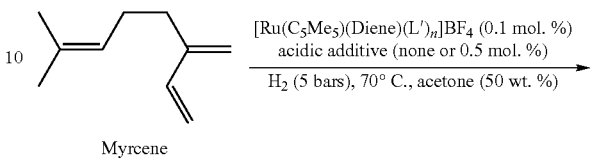

Myrcene

[Ru(C$_5$Me$_5$)(Diene)(L')$_n$]BF$_4$ (0.1 mol. %)
acidic additive (none or 0.5 mol. %)
H$_2$ (5 bars), 70° C., acetone (50 wt. %)

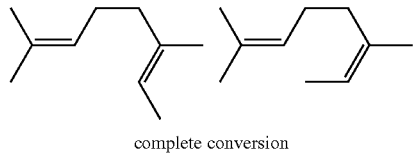

complete conversion

| Diene | Presence of Maleic acid | 1,4-Selectivity | Ratio "cis"-alkene/"trans"-alkene |
|---|---|---|---|
| 1,3-COD | no | >98% | 52/48 |
| 1,3-COD | yes | >98% | 95/5 |
| NBD | no | >97% | 53/47 |
| NBD | yes | >97% | 95/5 |
| 1,5-hexadiene | no | >96% | 54/46 |
| 1,5-hexadiene | yes | >96% | 96/4 |

L' being acetone in its ketone or enol form (n: 0 or 1)

TABLE 7 influence of the acidic additive and of its presence on hydrogenation selectivity influence of the ligand L reaction type:

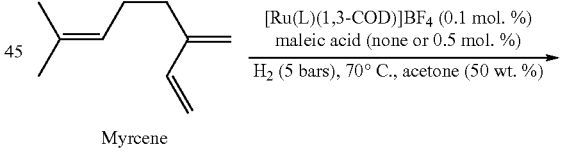

Myrcene

[Ru(L)(1,3-COD)]BF$_4$ (0.1 mol. %)
maleic acid (none or 0.5 mol. %)
H$_2$ (5 bars), 70° C., acetone (50 wt. %)

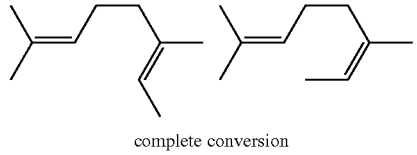

complete conversion

| L | Presence of Maleic acid | 1,4-Selectivity | Ratio "cis"-alkene/"trans"-alkene |
|---|---|---|---|
| C$_5$Me$_5$ | no | >98% | 52/48 |
| C$_5$Me$_5$ | yes | >98% | 95/5 |
| 1,2-(iPr)$_2$C$_5$Me$_3$ | no | >99% | 65/35 |
| 1,2-(iPr)$_2$C$_5$Me$_3$ | yes | >99% | 97.5/2.5 |
| 1,2,4-(tBu)$_3$C$_5$H$_2$ | no | >99% | 85/15 |
| 1,2,4-(tBu)$_3$C$_5$H$_2$ | yes | >99% | 98.5/1.5 |
| (Me$_3$SiO)C$_5$Me$_4$ | no | >99% | 58/42 |
| (Me$_3$SiO)C$_5$Me$_4$ | yes | >99% | 90/10 |

TABLE 8 influence of the acidic additive and of its presence on hydrogenation selectivity influence of the anion X reaction type:

Myrcene → [Ru(C5Me5)(1,3-COD)]X (0.1 mol. %), maleic acid (none or 0.5 mol. %), H2 (5 bars), 70° C., acetone (50 wt. %)

complete conversion

| X | Presence of Maleic acid | 1,4-Selectivity | Ratio "cis"-alkene/"trans"-alkene |
|---|---|---|---|
| $BF_4^-$ | no | >98% | 52/48 |
| $BF_4^-$ | yes | >98% | 95/5 |
| $ClO_4^-$ | no | >95% | 88/12 |
| $ClO_4^-$ | yes | >96% | 92/8 |
| $CF_3SO_3^-$ | no | >92% | 90/10 |
| $CF_3SO_3^-$ | yes | >94% | 92/8 |
| $PF_6^-$ | no | >94% | 92/8 |
| $PF_6^-$ | yes | >98% | 96/4 |

TABLE 9 influence of the acidic additive and of its presence on hydrogenation selectivity influence of the ligand L reaction type:

2,4-hexadienol → [Ru(L)(1,3-COD)]BF4 (0.05 mol. %), (C6H5)2P(O)(OH) (none or 0.25 mol. %), H2 (5 bars), 70° C., acetone (50 wt. %)

complete conversion

| L | Presence of $(C_6H_5)_2P(O)(OH)$ acid | 1,4-Selectivity | Ratio "cis"-alkene/"trans"-alkene |
|---|---|---|---|
| $C_5Me_4H$ | no | >98% | 90/10 |
| $C_5Me_4H$ | yes | >98% | 97.5/2.5 |
| $C_5Et_5$ | no | >98% | 88/12 |
| $C_5Et_5$ | yes | >98% | 98/2 |
| 1,2-$(iPr)_2C_5Me_3$ | no | >99% | 80/20 |
| 1,2-$(iPr)_2C_5Me_3$ | yes | >99% | 95/5 |
| 1,2,4-$(tBu)_3C_5H_2$ | no | >99% | 50/50 |
| 1,2,4-$(tBu)_3C_5H_2$ | yes | >99% | 70/30 |
| $(Me_3SiO)C_5Me_4$ | no | >99% | 85/15 |
| $(Me_3SiO)C_5Me_4$ | yes | >99% | 95/5 |

TABLE 10 influence of the acidic additive and of its presence on hydrogenation selectivity influence of the Diene reaction type:

2,4-hexadienol → [Ru(C5Me5)(Diene)(L')n]BF4 (0.05 mol. %) (C6H5)2P(O)(OH) (none or 0.25 mol. %), H2 (5 bars), 70° C., acetone (50 wt. %)

complete conversion

| L | Presence of $(C_6H_5)_2P(O)(OH)$ acid | 1,4-Selectivity | Ratio "cis"-alkene/"trans"-alkene |
|---|---|---|---|
| NBD | no | >98% | 90/10 |
| NBD | yes | >98% | 98/2 |
| dimethyllbutadiene | no | >98% | 90/10 |
| dimethyllbutadiene | yes | >98% | 98/2 |
| 1,5-hexadiene | no | >99% | 90/10 |
| 1,5-hexadiene | yes | >99% | 98/2 |
| 2,4-hexadienylacetate | no | >98% | 90/10 |
| 2,4-hexadienylacetate | yes | >98% | 98/2 |

L' being acetone in its ketone or enol form (n: 0 or 1)

The invention claimed is:

1. A process for the catalytic reduction by 1,4-hydrogenation, using molecular $H_2$, of a $C_5$-$C_{22}$ conjugated diene of formula

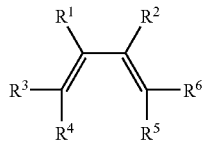 (I)

wherein $R^1$, $R^2$, $R^3$, $R^4$, $R^5$ and $R^6$ represent, simultaneously or independently from each other, a hydrogen atom or a $C_1$-$C_{12}$ alkyl or alkenyl group optionally substituted;
one of $R^2$ or $R^6$ may also represent a $C_1$-$C_{12}$ alkoxy or acyloxy group optionally substituted; and
$R^1$ and $R^3$, or $R^3$ and $R^4$, or $R^2$ and $R^6$, or $R^6$ and $R^5$, or $R^4$ and $R^5$, taken together, may form a $C_{2-16}$ alkanediyl or de-conjugated alkenediyl group, optionally substituted;
into the corresponding alkene, of formula

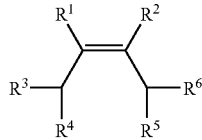 (II)

wherein $R^1$ to $R^6$ have the same meaning as for the compound of formula (I), and wherein the isomer having the $R^1$ and $R^2$ groups in a cis configuration is predominant;
wherein said process is carried out in the presence of
at least one ruthenium catalyst or pre-catalyst of formula

[Ru(L)(Diene)(L')n]X (III)

wherein L represents a C5-C25 substituted cyclopentadienyl ligand, Diene represents a C4-C22 diene and X represents a non coordinated anion, n represents 2, 1 or 0 and L' represents a solvent; and at least an acidic additive selected from the group consisting of:

a compound of formula $R^{14}{}_{(3-x)}MO(OH)_x$, wherein $R^{14}$ is a $R^{14'}$ or $R^{14'}O$ group wherein $R^{14'}$ is a $C_1$-$C_{10}$ group, M is P or As and x is 1 or 2; and a boron derivative of formula $R^{14}B(OH)_2$, wherein $R^{14}$ is as defined above; and phenol or a phenol substituted by up to three $C_1$-$C_4$ alkyl, alkoxy or carboxylic groups, nitro groups or halogen atoms; and a $C_1$-$C_{12}$ mono-carboxylic non-amino acid; and a HOOCCH=CHCOOH di-acid, and the tetronic acid;

provided that the processes wherein compound (I) is sorbol and compound (III) is of formula [Ru(Cp*)(COD)]X are excluded.

2. A process according to claim 1, wherein L is a $C_6$-$C_{25}$ compound of formula

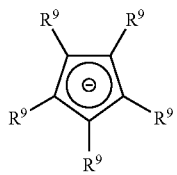

(IV)

wherein each R9 represents, simultaneously or independently from each other, a hydrogen atom, a phenyl group optionally substituted, or a C1-C10 alkyl or alkenyl group optionally substituted; and one or two of said groups R9 can be a CF3 group, a OSiR113, OCOR10, COR10 or COOR10 group, R11 representing a C1-C11 alkyl group, R10 representing a R11 or CF3 group or a phenyl group optionally substituted; and at least one R9 is an alkyl group; two adjacent R9 can be bound together to form a C2-C10 alkanediyl group.

3. A process according to claim 2, wherein two $R^9$ represent, simultaneously or independently from each other, a hydrogen atom or a $C_1$-$C_4$ alkyl group and the three other $R^9$ represent, simultaneously or independently, a $C_1$-$C_4$ alkyl group.

4. A process according to claim 2, wherein four $R^9$ represent, simultaneously or independently from each other, a hydrogen atom or a $C_1$-$C_4$ alkyl group and one $R^9$ represents OSiR$^{11}{}_3$, $R^{11}$ representing a $C_1$-$C_4$ alkyl group, and at least one $R^9$ is an alkyl group.

5. A process according to claim 1, wherein Diene is a conjugated or non conjugated cyclic $C_6$-$C_{12}$ alkadiene.

6. A process according to claim 1, wherein X is $ClO_4^-$, $R^{12}SO_3^-$, wherein $R^{12}$ is a chlorine or fluorine atom or a $C_1$-$C_8$ fluoroalkyl or fluoroaryl group, $BF_4^-$, $PF_6^-$, $SbCl_6^-$, $SbF_6^-$, or $BR^{13}{}_4^-$, wherein $R^{13}$ is a phenyl group optionally substituted by one to five halide atoms or methyl or $CF_3$ groups.

7. A process according to claim 1, wherein said mono-carboxylic acid is selected from the group consisting of a carboxylic acid of formula $R^{15}COOH$, wherein $R^{15}$ represents:

a halogenated or per-halogenated $C_1$-$C_8$ hydrocarbon group;

a $R^{16}CH(OR^{16})$ group, $R^{16}$ being a hydrogen atom or a $C_1$-$C_6$ hydrocarbon group;

a $C_1$-$C_{12}$ hydrocarbon group, optionally substituted by one or two ether or ester groups;

the optional substituent being one, two or three $C_1$-$C_4$ alkyl, alkoxy or carboxylic groups, or nitro groups or halogen atoms.

8. A process according to claim 7, wherein said acidic additive is selected from the group consisting of a compound of formula $R^{14}{}_2MO(OH)$ or $R^{14}MO(OH)_2$, wherein $R^{14}$ is a $C_1$-$C_6$ alkyl or alkoxyl group or a $C_6$-$C_8$ phenyl or phenoxyl and M is P or As; and maleic or glycolic acid and an halogenated or per-halogenated $C_1$-$C_7$ mono-carboxylic acid.

9. A process according to claim 1, wherein the conjugated diene of formula (I) is a compound of formula (I')

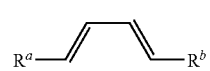

(I')

wherein $R^a$ represents a linear, branched or cyclic $C_1$-$C_8$ alkyl or alkenyl group; and $R^b$ represents a $(CH_2)_nX$ group, n representing 0, 1, 2 or 3, X representing a CHO, OH, $OCOR^c$, $OR^c$ or $COOR^c$ group, $R^c$ being a $C_1$-$C_8$ alkyl or alkenyl group; or of formula (I''):

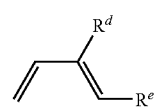

(I'')

wherein $R^d$ and $R^e$ represent a hydrogen atom or a $C_1$-$C_8$ alkyl or alkenyl group, optionally substituted by a OH, $OCOR^f$, $OR^f$ or $COOR^f$ group, $R^f$ being a $C_1$-$C_8$ alkyl or alkenyl group, provided that $R^d$ and $R^e$ do not represent each a hydrogen atom.

* * * * *